United States Patent
Chen et al.

(10) Patent No.: US 7,598,402 B2
(45) Date of Patent: *Oct. 6, 2009

(54) PROCESS FOR SYNTHESIZING TRIOXYMETHYLENE USING IONIC LIQUID

(75) Inventors: Jing Chen, Lanzhou (CN); Heyuan Song, Lanzhou (CN); Chungu Xia, Lanzhou (CN); Zhonghua Tang, Lanzhou (CN); Xinzhi Zhang, Beijing (CN); Zhen Li, Lanzhou (CN); Enxiu Guo, Beijing (CN)

(73) Assignees: Lanzhou Institute of Chemical Physics Chinese Academy of Sciences, Lanzhou (CN); Blue Diamond International Co., Ltd., Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 12/016,837

(22) Filed: Jan. 18, 2008

(65) Prior Publication Data

US 2008/0293954 A1    Nov. 27, 2008

(51) Int. Cl.
*C07D 323/06* (2006.01)
(52) U.S. Cl. .................................... 549/368
(58) Field of Classification Search ................. 549/368
See application file for complete search history.

(56) References Cited

U.S. PATENT DOCUMENTS

| | | | |
|---|---|---|---|
| 5,929,257 A * | 7/1999 | Kashihara et al. | 549/368 |
| 5,962,702 A | 10/1999 | Morishita | |
| 6,201,136 B1 * | 3/2001 | Reichl et al. | 549/368 |
| 6,388,102 B2 * | 5/2002 | Schweers et al. | 549/368 |
| 7,244,854 B2 | 7/2007 | Xia et al. | |

OTHER PUBLICATIONS

Xin-Yu et al., "Cyclotrimerization of Aliphatic Aldehydes Catalyzed by Ionic Liquids", Chinese Journal of Chemistry, 24 1066-1068 (2006).

Auge et al., "A Convenient Solvent-Free Preparation of 1,3,5-trioxanes", Tetrahedron. Letters 43, 7919-7920 (2002).

* cited by examiner

*Primary Examiner*—Janet L. Andres
*Assistant Examiner*—Raymond Covington
(74) *Attorney, Agent, or Firm*—Heslin Rothenberg Farley & Mesiti P.C.

(57) ABSTRACT

The present invention relates to a process for synthesizing trioxymethylene, wherein an aqueous solution of formaldehyde is used as the reactant; and an acidic ionic liquid in an amount of from 0.01 to 10 wt % is used as a catalyst.

11 Claims, No Drawings

PROCESS FOR SYNTHESIZING TRIOXYMETHYLENE USING IONIC LIQUID

CROSS REFERENCE TO RELATED APPLICATIONS

This application claims priority to Chinese application number 200710105042.1, filed on May 22, 2007, the contents of which are incorporated herein by reference.

FIELD OF THE INVENTION

The present invention relates to the catalytic synthesis of trioxymethylene using an acidic ionic liquid as the catalyst. Trioxymethylene is an important industrial material, especially useful as a raw material for producing polyoxymethylene resin and widely used as a substitute for formaldehyde.

BACKGROUND OF THE INVENTION

Trioxymethylene is a white crystal with stable properties. It is used as a stabilizer, a fumigant, an insecticide, a molding material, a binder, an antiseptic, an antibacterial agent and the like. It can be converted into formaldehyde via depolymerization and therefore can be used in almost all the reactions that use formaldehyde as a reactant, especially in cases where anhydrous formaldehyde is used. Trioxymethylene is the raw material for the synthesis of polyoxymethylene, one of the three most important general engineering plastics, and the only one that does not rely on petroleum resources.

Trioxymethylene has been used as a monomer to synthesize polyoxymethylene in the worldwide production of polyoxymethylene. Processes for the synthetic production of trioxymethylene are currently needed.

SUMMARY OF THE INVENTION

The present invention provides a process for synthesizing trioxymethylene from formaldehyde through catalytic polymerization using an ionic liquid as a catalyst.

The present invention involves a reaction as shown below:

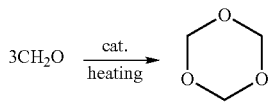

The present application provides a process for synthesizing trioxymethylene, wherein an aqueous solution of formaldehyde is used as the reactant; and an acidic ionic liquid in an amount of from 0.01 to 10 wt % is used as catalyst. The concentration of the aqueous solution of formaldehyde is preferably between 37-70%.

The cation moiety of the catalyst used in the present invention can be selected from imidazole cations, pyridine cations, quaternary ammonium cations, quaternary phosphine cations, and the like.

The anion moiety of the catalyst can be selected from p-toluene sulfonic acid, trifluoromethyl sulfonate, methylsulfonate, bisulfate, sulfate, formate, acetate, trifluoroacetate, phosphate, monohydrogen phosphate, dihydrogen phosphate, tetrafluoborate, hexafluorophosphate, bis(methyl sulfonyl)imide, bis(trifluoromethylsulfonyl)imide, trifluoromethyl imine, chlorine ion, bromine ion, monomethyl sulfate anion, monoethyl sulfate anion, and the like.

In preferred embodiments of the invention, the amount of catalyst present in the reaction mixture is kept between 0.01 wt % and 10 wt %.

In some embodiments of the invention the catalysts used may comprise one or more imidazole cations selected from:

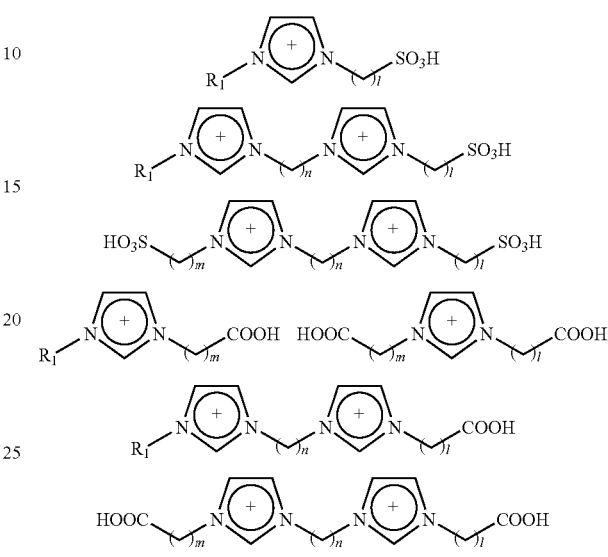

wherein m is an integer between 0-15, n is an integer between 0-10 and l is an integer between 0-15; and $R_1$ is an alkyl or aryl group.

Pyridine cations of the catalyst can be selected from:

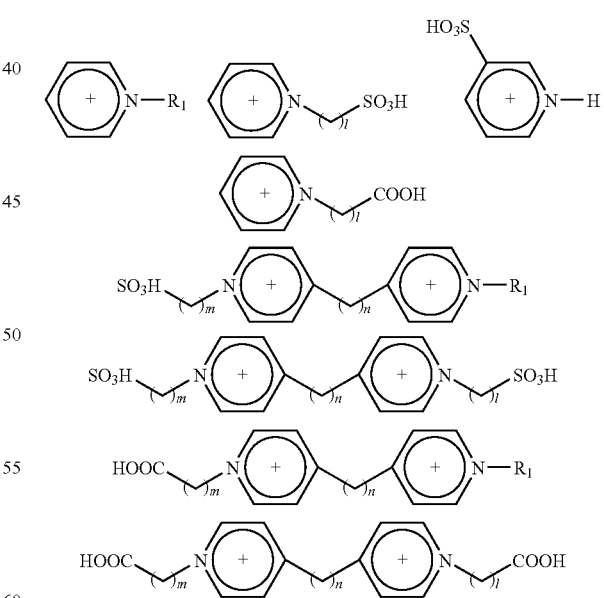

wherein m is an integer between 0-15, n is an integer between 0-2, l is an integer between 0-15; and $R_1$ is an alkyl or aryl group.

Quaternary ammonium cations of the catalyst can be selected from:

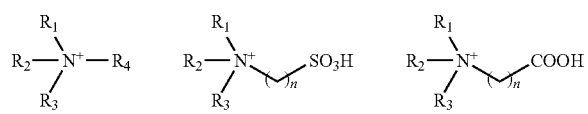

wherein n is an integer between 0-15; and $R_1$, $R_2$, $R_3$ and $R_4$ are selected from alkyl and aryl groups.

Quaternary phosphine cations of the catalyst can be selected from

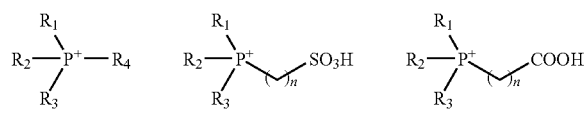

wherein n is an integer between 0-15; and $R_1$, $R_2$, $R_3$ and $R_4$ are selected from a alkyl and aryl groups.

Anions of the catalyst can be selected from:
$CH_3PhSO_3^-$, $CF_3SO_3^-$, $HSO_4^-$—$SO_4^{2-}$, $HCOO^-$, $CH_3COO^-$, $CF_3COO^-$, $PO_4^{3-}$, $HPO_4^{2-}$, $H_2PO_4^-$ and $N(CH_3SO_2)_2^-$.

During the preparation of the catalyst, the acids providing anions can include p-toluene sulfonic acid (98%), trifluoromethyl sulfonic acid (98%), methylsulfonic acid (99%), sulfuric acid (98%), formic acid (90%), glacial acetic acid (99.5%), trifluoroacetic acid (99.5%) and phosphoric acid (85%). Amines such as methyl sulfonylimide can also be used to provide anions for the catalyst used in the present invention.

The raw material used in the present invention is a dealcoholized formaldehyde solution, with a concentration of 37-70%.

A rectification device is used according to the present invention, wherein the rectifying section utilizes a glass packed column with an inner diameter of 30 mm and a filling height of 0.3 m and the packing material is the θ 2.0 mm×2.0 mm 316 L type stainless steel Rasching ring. The number of the column plates is about 7-8. And the reactor is a 250 mL of three-necked flask. The condenser at the top of the rectifying section is an electromagnetic relay type condenser and the reflux ratio is controlled and adjusted by a time program controller.

The invention provides a number of advantages. The invention provides a low cost catalytic system to produce trioxymethylene with high selectivity and low corrosion.

The invention uses an ionic liquid as a catalyst that is easy to prepare and has high catalytic activity in the synthesis of trioxymethylene from formaldehyde. Another advantage is that the reaction mixture provides trioxymethylene at high concentration with superior selectivity. Another advantage is that there are reduced amounts of by-products such as methanol, formic acid, methylal and the like in the final reaction mixture. The invention also provides for a raw material, formaldehyde solution, that can be used with a wide concentration range, i.e, from 37 to 70% and for a low amount of ionic liquid catalyst, i.e., about 0.01~10% by weight.

Other advantages include low corrosion to the reaction apparatus and therefore there is no special requirements are needed for the reaction apparatus and that the catalyst can be circulated in the reaction apparatus for continuous use. The reaction does not have as much caking as in other systems when reaction is interrupted in the reactor, therefore cost of labor and financial resources to clean the reactor are avoided.

EXAMPLES OF THE INVENTION

Formulas of the catalysts used in the following examples of the present invention are as follows:

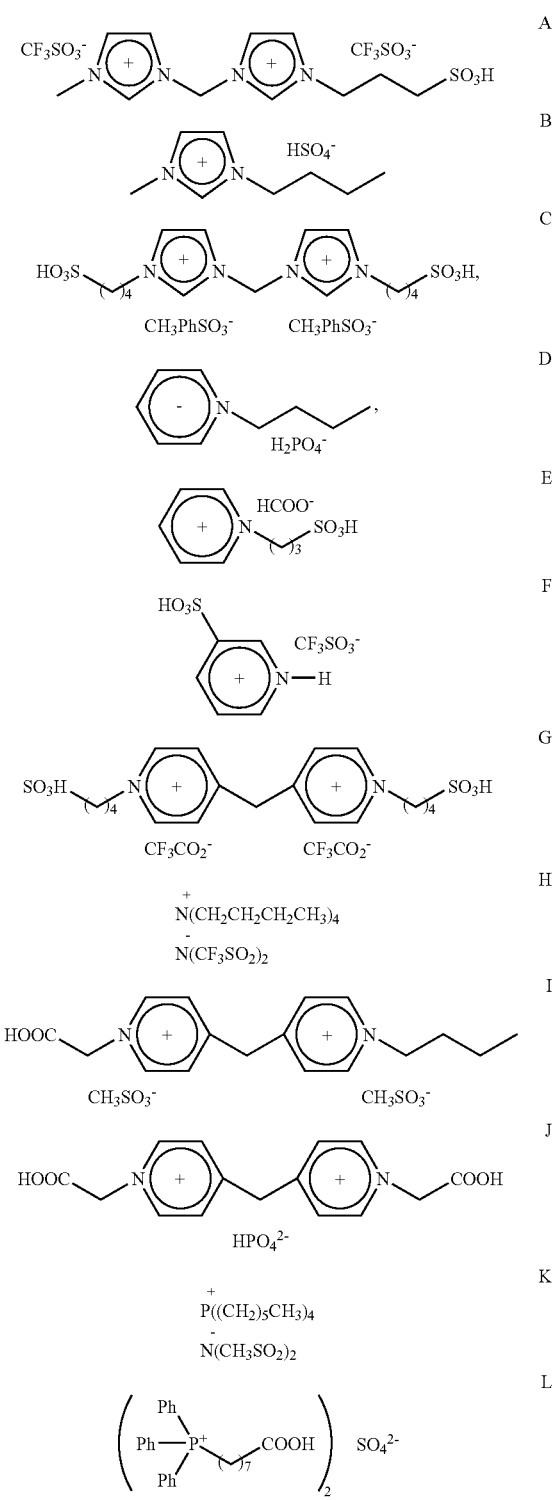

-continued

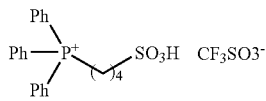
M

Example 1

100 g of 60.1% formaldehyde solution (containing 1.2% of methanol) and 4.1 g of catalyst A were added sequentially into a 250 ml reactor. The reaction mixture was heated and refluxed sufficiently for 4 h, the reflux ratio was set to R=2. Formaldehyde, trioxymethylene and an aqueous azeotropic mixture were evaporated off from the top of the reactor. At the same time, 50 g of 60.1% formaldehyde solution was added into the reactor at a feeding rate of 0.5 mL/min. The temperature at the bottom of the rectifying still was 96-97° C. and the temperature at the top of the tower was 92-93° C. After 3 hours of reaction, chromatographic analysis indicated that the distillate contained 17.8% of trioxymethylene, 0.9% of methanol and 0.2% of methylal.

Example 2

The same as in example 1, except that 2.0 g of catalyst B was added into 200 g of 50.3% formaldehyde solution (containing 1.5% of methanol). The temperature at the bottom of the rectifying still was 96-97° C. and the temperature at the top of the tower was 92-93° C. The distillate contained 18.2% of trioxymethylene, 1.7% of methanol and 0.8% of methylal.

Example 3

The same as in example 1, except that 2.5 g of catalyst C was added into 110 g of 50.3% formaldehyde solution (containing 1.5% of methanol). The temperature at the bottom of the rectifying still was 96-97° C., and the temperature at the top of the tower was 91-92° C. The distillate contained 26.1% of trioxymethylene, 1.1% of methanol and 0.3% of methylal.

Example 4

The same as in example 1, except that 1.0 g of catalyst D was added into 200 g of 51.3% formaldehyde solution (containing 0.3% of methanol). The temperature at the bottom of the rectifying still was 96-97° C., and the temperature at the top of the tower was 91-92° C. The distillate contained 30.5% of trioxymethylene, 0.4% of methanol, while no methylal was detected.

Example 5

The same as in example 1, except that 1.7 g of catalyst E was added into 100 g of 50.3% formaldehyde solution (containing 1.7% of methanol). The temperature at the bottom of the rectifying still was 96.5° C., and the temperature at the top of the tower was 93-94° C. The distillate contained 19.2% of trioxymethylene, 1.9% of methanol and 1.2% of methylal.

Example 6

The same as in example 1, except that 2.6 g of catalyst F was added into 100 g of 50.3% formaldehyde solution (containing 1.7% of methanol). The temperature at the bottom of the rectifying still was 96.5° C., and the temperature at the top of the tower was 93-94° C. The distillate contained 16.4% of trioxymethylene, 2.0% of methanol and 1.1% of methylal.

Example 7

The same as in example 1, except that 3.1 g of catalyst G was added into 100 g of 50.3% formaldehyde solution (containing 1.7% of methanol). The temperature at the bottom of the rectifying still was 96.5° C., and the temperature at the top of the tower was 93-94° C. The distillate contained 20.2% of trioxymethylene, 1.9% of methanol and 1.2% of methylal.

Example 8

The same as in example 1, except that 3.7 g of catalyst H was added into 100 g of 51.4% formaldehyde solution (containing 0.9% of methanol). The temperature at the bottom of the rectifying still was 96-97° C., and the temperature at the top of the tower is 92-93° C. The distillate contained 23.4% of trioxymethylene, 1.0% of methanol and 0.8% of methylal.

Example 9

The same as in example 1, except that 1.8 g of catalyst I was added into 100 g of 50.3% formaldehyde solution (containing 1.7% of methanol). The temperature at the bottom of the rectifying still was 96.5-97° C., and the temperature at the top of the tower was 93-94° C. The distillate contained 18.3% of trioxymethylene, 1.9% of methanol and 1.0% of methylal.

Example 10

The same as in example 1, except that 1.2 g of catalyst J was added into 150 g of 51.4% formaldehyde solution (containing 0.9% of methanol). The temperature at the bottom of the rectifying still was 97° C., and the temperature at the top of the tower was 91-92° C. The distillate contained 28.5% of trioxymethylene, 1.0% of methanol, while no methylal was detected.

Example 11

The same as in example 1, except that 2.0 g of catalyst K was added into 100 g of 50.3% formaldehyde solution (containing 1.7% of methanol). The temperature at the bottom of the rectifying still was 96.5-97° C., and the temperature at the top of the tower was 93-94° C. The distillate contained 17.3% of trioxymethylene, 1.9% of methanol and 0.8% of methylal.

Example 12

The same as in example 1, except that 1.2 g of catalyst L was added into 100 g of 51.4% formaldehyde solution (containing 0.9% of methanol). The temperature at the bottom of the rectifying still was 96-97° C., and the temperature at the top of the tower was 93-94° C. The distillate contained 15.5% of trioxymethylene, 1.9% of methanol and 0.4% of methylal.

Example 13

The same as in example 1, except that 1.5 g of catalyst M was added into 100 g of 51.4% formaldehyde solution (containing 0.9% of methanol). The temperature at the bottom of the rectifying still was 97° C., and the temperature at the top of the tower was 93-94° C. The distillate contained 17.2% of trioxymethylene, 1.1% of methanol and 0.5% of methylal.

Example 14

The same as in example 1, except that 2.0 g of catalyst J was weighed and added into 200 g of 52.1% formaldehyde solution (containing 0.9% of methanol). The temperature at the bottom of the rectifying still was 96-97° C., and the temperature at the top of the tower was 92-93° C. After 4 hours of reaction, chromatographic analysis indicated that the distillate contained 31.7% of trioxymethylene, 1.1% of methanol, while no methylal was detected. And the content of formic acid in the final reaction mixture was determined by acid-base titration to be 119 ppm.

Example 15

The same as in example 1, except that 2.0 g of catalyst C was weighed and added into 200 g of 38.8% formaldehyde solution (containing 1.8% of methanol). The temperature at the bottom of the rectifying still was 96.5° C., and the temperature at the top of the tower was 94° C. After 4 hours of reaction, chromatographic analysis indicated that the distillate contained 21.8% of trioxymethylene, 2.3% of methanol and 1.4% of methylal. And the content of formic acid in the final reaction mixture was determined by acid-base titration to be 217 ppm.

Example 16

The same as in example 1, except that 1.1 g of catalyst J was weighed and added into 10 g of 52.1% formaldehyde solution (containing 0.9% of methanol). The temperature at the bottom of the rectifying still was 96-97° C., and the temperature at the top of the tower was 92-93° C. After 1 hour of reaction, chromatographic analysis indicated that the distillate contained 22.0% of trioxymethylene. Then the power was turned off and the reactor was cooled down. After 48 hours, a little polymer (white solid) was found at the bottom of the reactor. With increasing of the temperature, the reactor bottom became clear again at a temperature of about 85° C. A sample was taken when the temperature at the reactor bottom reached 96° C. The chromatographic analysis indicated that the distillate contained 26.1% of trioxymethylene, 1.3% of methanol and 0.2% of methylal.

What is claimed is:

1. A process for synthesizing trioxymethylene, comprising forming a reaction mixture by reacting an aqueous solution of formaldehyde with an acidic ionic liquid as a catalyst, wherein the acidic ionic liquid is present in an amount of from 0.01 to 10 wt % of the reaction mixture and has a cation moiety and an anion moiety, wherein the cation moiety of the catalyst is selected from imidazole cations and pyridine cations.

2. A process according to claim 1, wherein the anion moiety of the catalyst is selected from p-toluene sulfonic acid, trifluoromethyl sulfonate, methylsulfonate, bisulfate, sulfate, formate, acetate, trifluoroacetate, phosphate, monohydrogen phosphate, dihydrogen phosphate, tetra-fluoborate, hexafluorophosphate, bis(methylsulfonyl)imide, bis(trifluoromethylsulfonyl)imide, trifluoromethyl imine, chlorine ion, bromine ion, monomethyl sulfate anion, and monoethyl sulfate anion.

3. A process according to claim 1, wherein the imidazole cations are selected from

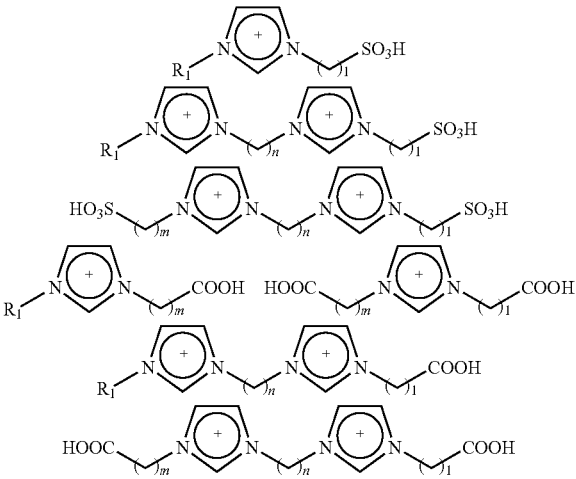

wherein m is an integer between 0-15, n is an integer between 0-10, 1 is an integer between 0-15; and $R_1$ is selected from alkyl and aryl groups.

4. A process according to claim 1, wherein the pyridine cations are selected from

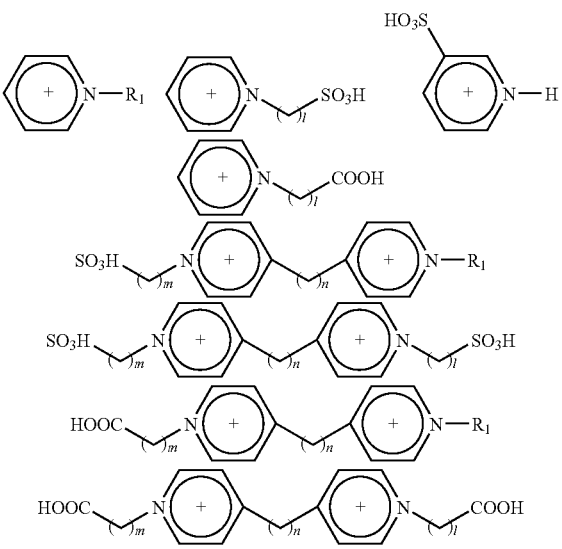

wherein m is an integer between 0-15, n is an integer between 0-2, 1 is an integer between 0-15; and $R_1$ is selected from alkyl and aryl groups.

5. A process according to claim 2, wherein the anion moiety of the catalyst is selected from:

$CH_3PhSO_3^-$, $CF_3SO_3^-$, $HSO_4^-$, $SO_4^{2-}$, $HCOO^-$, $CH_3COO^-$, $CF_3COO^-$, $PO_4^{3-}$, $HPO_4^{2-}$, $H_2PO_4^-$, $N(CH_3SO_2)_2^-$.

6. A process according to any one of claims 1, 2, 3, 4, or 5, wherein the acidic ionic liquid catalyst is used in an amount from 0.01 to 10 wt %.

7. A process according to any one of claims 1, 2, 3, 4, or 5, wherein the concentration of the aqueous solution of formaldehyde is from 37 to 70%.

8. A process according to claim 1, wherein the reaction takes place in a rectification device.

9. A process according to claim 8, wherein the rectification device is a continuously feeding rectification device.

10. A process according to claim 8, wherein the temperature at the bottom of the rectifying still is from 96 to 98° C., and the temperature at the top of the rectification tower is from 92 to 94° C.

11. A process according to claim 8, wherein the rectification device has from 5 to 16 theoretical plates.

* * * * *